(12) United States Patent
Ookawa

(10) Patent No.: US 8,797,032 B2
(45) Date of Patent: Aug. 5, 2014

(54) MAGNETIC RESONANCE IMAGING APPARATUS AND MAGNETIC RESONANCE IMAGING METHOD

(75) Inventor: Masashi Ookawa, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 436 days.

(21) Appl. No.: 13/175,120

(22) Filed: Jul. 1, 2011

(65) Prior Publication Data

US 2012/0001635 A1  Jan. 5, 2012

(30) Foreign Application Priority Data

Jul. 2, 2010   (JP) ................................ 2010/152213
Jun. 13, 2011  (JP) ................................ 2011/131069

(51) Int. Cl.
*G01V 3/00* (2006.01)
(52) U.S. Cl.
USPC .......................................... 324/314; 324/315
(58) Field of Classification Search
USPC ................. 324/314, 315, 320, 309, 307, 300
See application file for complete search history.

(56) References Cited

U.S. PATENT DOCUMENTS

| | | | | |
|---|---|---|---|---|
| 4,789,833 A | * | 12/1988 | Nishimura | 324/320 |
| 6,184,684 B1 | * | 2/2001 | Dumoulin et al. | 324/318 |
| 6,242,915 B1 | * | 6/2001 | Hurd | 324/309 |
| 7,026,814 B2 | * | 4/2006 | Bordon et al. | 324/303 |
| 8,188,741 B2 | * | 5/2012 | Sakakura | 324/318 |
| 8,305,079 B2 | * | 11/2012 | Iwasa et al. | 324/315 |

FOREIGN PATENT DOCUMENTS

| | | |
|---|---|---|
| CN | 1455874 A | 11/2003 |
| JP | 5-76514 | 3/1993 |
| JP | 2005-288025 | 10/2005 |

OTHER PUBLICATIONS

Office Action dated Nov. 26, 2012 in CN 201110185729.7.

* cited by examiner

*Primary Examiner* — Louis Arana
(74) *Attorney, Agent, or Firm* — Nixon & Vanderhye PC

(57) ABSTRACT

The temperature of an MRI gradient magnetic field coil unit is measured at least two times. Shift data indicating a center magnetic resonance frequency of a hydrogen atom in response to variation of the gradient coil temperature is stored in advance. Estimated shift of the center frequency based on the measurement result is determined and the center frequency of an RF NMR excitation pulse is corrected based on the estimated shift.

21 Claims, 8 Drawing Sheets

MAGNETIC RESONANCE IMAGING APPARATUS AND MAGNETIC RESONANCE IMAGING METHOD

CROSS-REFERENCE TO RELATED APPLICATION(S)

This application is based upon and claims the benefit of priority from Japanese Patent Application No. 2010-152213, filed on Jul. 2, 2010, and Japanese Patent Application No. 2011-131069 filed on Jun. 13, 2011; the entire contents of which are incorporated herein by reference.

BACKGROUND OF THE INVENTION

1. Field of the Invention

Embodiments described herein relate generally to a magnetic resonance imaging apparatus and a magnetic resonance imaging method.

2. Description of the Related Art

MRI is an imaging method which magnetically excites nuclear spin of an object (a patient) set in a static magnetic field with an RF pulse having the Larmor frequency and reconstructs an image based on MR signals generated due to the excitation. The aforementioned MRI means magnetic resonance imaging, the RF pulse means a radio frequency pulse, and the MR signal means a nuclear magnetic resonance signal.

An MRI apparatus has a gradient magnetic field coil that applies a gradient magnetic field to an imaging space in which an object is placed, thereby providing an MR signal with spatial positional information. The gradient magnetic field coil generates significant heat during imaging because of a pulse current repeatedly supplied thereto. As the temperature of the gradient magnetic field coil rises, the temperature of an iron shim nearby also rises, and the magnetic permeability of the iron shim varies. As a result, the magnetic field in the imaging space varies, and the center frequency of the magnetic resonance of hydrogen atoms in the object also varies.

Japanese Patent Laid-Open No. 2005-288025 discloses a known conventional technique relating to detection of the variation of the resonance frequency and the temperature of the iron shim and the surroundings.

According to the Japanese Patent Laid-Open No. 2005-288025, inhomogeneity of a static magnetic field disturbed by the temperature variation of the iron shim is detected, and a variation of the resonance frequency in the imaging cross section is estimated based on the temperature variation. Then, the frequency of a reference clock of a control system is modified to follow the variation of the resonance frequency, and respective units are controlled based on the modified reference clock, thereby reducing the effect of the disturbance in the static magnetic field homogeneity.

The center frequency of an RF pulse, such as a fat suppression prepulse and a 90° excitation pulse, is set based on the Larmor frequency of hydrogen atoms that depends on the intensity of the static magnetic field during an imaging preparation step, such as a prescan step. However, if the center frequency of the magnetic resonance of the hydrogen atoms in a fat tissue shifts because of the heat generation of the gradient magnetic field coil during imaging after the conditions concerning the fat suppression prepulse is set in the imaging preparation step, the effect of the fat suppression can be inadequate.

In particular, in seriography, such as dynamic imaging, which takes a long time, the heat generation of the gradient magnetic field coil can increase with the time elapsed from the start of imaging, and accordingly, the shift of the center frequency of the magnetic resonance of hydrogen atoms can increase. If this occurs, images collected at later points in time may be more degraded because of the degradation of the effect of the fat suppression prepulse.

DETAILED DESCRIPTION

Figure 1:
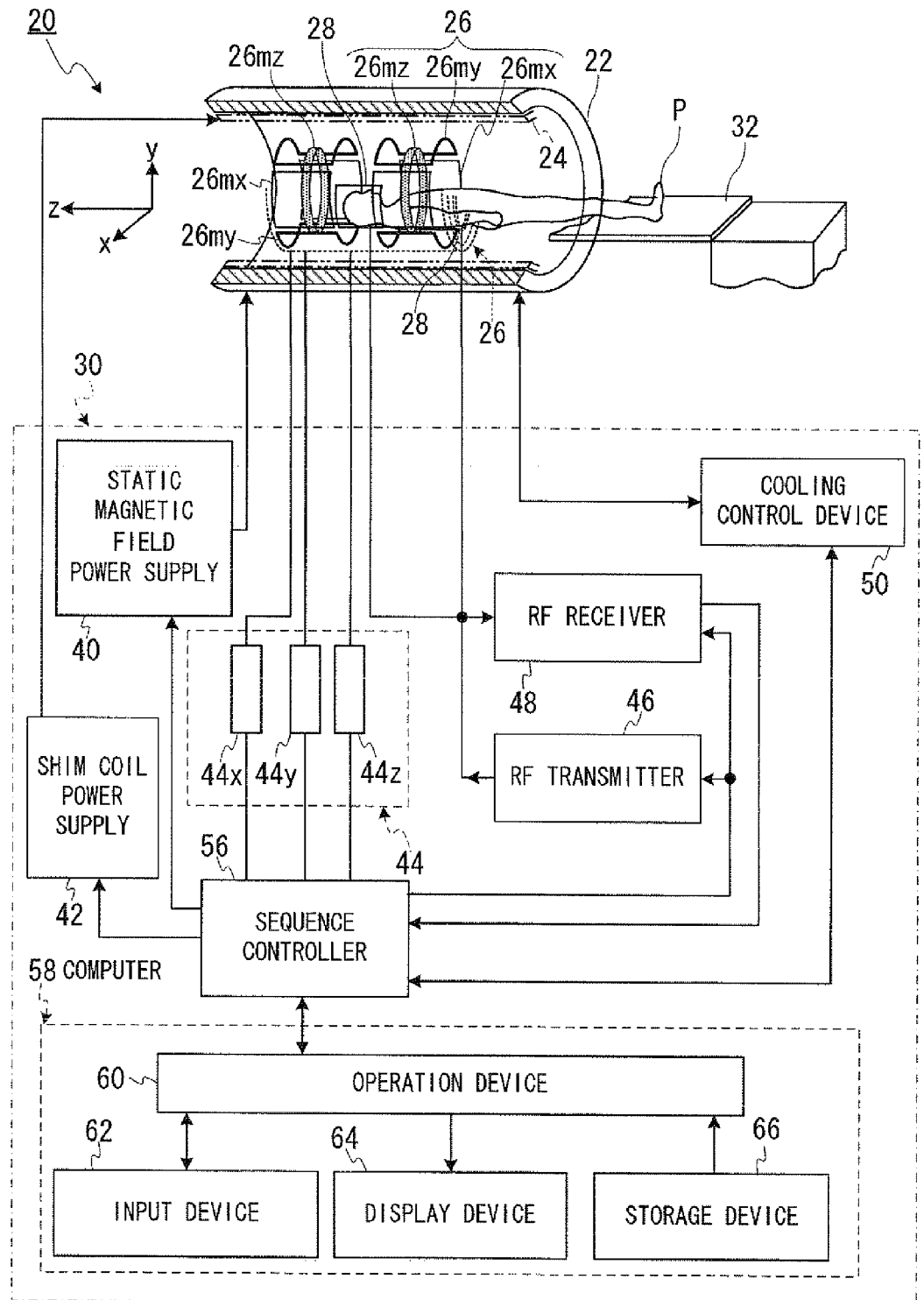
FIG. 1 is a block diagram showing general structure of the MRI apparatus of the present embodiment.

An embodiment of the present invention aims to provide an MRI technology which produces a high-quality image even if a center frequency of magnetic resonance of hydrogen atoms shifts because of heat generation of a gradient magnetic field coil, in a manner different from the conventional techniques. However, the present invention is not limited to this aim.

According to one embodiment, an MRI apparatus includes a gradient magnetic field coil unit, a temperature measuring unit, a data storing unit, a pulse setting unit and an imaging unit.

The gradient magnetic field coil unit generates a gradient magnetic field in an imaging space according to a current supplied thereto.

The temperature measuring unit measures a temperature of the gradient magnetic field coil unit at least two times at different timings.

The data storing unit stores shift data in advance of measurement by the temperature measuring unit. The shift data indicates a shift of a center frequency of magnetic resonance of a hydrogen atom in the imaging space in response to a variation of the temperature of the gradient magnetic field coil unit.

The pulse setting unit acquires a measurement result from the temperature measuring unit, determines an estimated shift of the center frequency of the magnetic resonance of the hydrogen atom according to the variation of the temperature of the gradient magnetic field coil unit based on the measurement result and the shift data, and corrects a center frequency of an RF pulse based on the estimated shift.

The imaging unit transmits the RF pulse corrected by the pulse setting unit, receives a magnetic resonance signal from an object in the imaging space, and generates image data of the object based on the magnetic resonance signal.

According to one embodiment, an MRI method includes the steps of:

(a) acquiring a measurement result by measuring a temperature of gradient magnetic field coil unit, which generates a gradient magnetic field in an imaging space according to a current supplied thereto, at least two times at different timings;

(b) referring to shift data indicating a shift of a center frequency of magnetic resonance of a hydrogen atom in the imaging space in response to a variation of the temperature of the gradient magnetic field coil unit;

(c) determining an estimated shift of the center frequency of the magnetic resonance of the hydrogen atom according to the variation of the temperature of the gradient magnetic field coil unit based on the measurement result and the shift data.

(d) correcting a center frequency of an RF pulse based on the estimated shift; and (e) generating image data of an object based on a magnetic resonance signal by transmitting the RF pulse whose center frequency is corrected and receiving the magnetic resonance signal from the object in the imaging space.

A magnetic resonance imaging apparatus and a magnetic resonance imaging method according to embodiments of the present invention will be described with reference to the accompanying drawings.

Note that the same reference numbers are given for identical components in each figure, and overlapping explanation is abbreviated.

(Configuration of the MRI Apparatus)

FIG. 1 is a block diagram showing general structure of the MRI apparatus 20 according to an embodiment of the present invention.

The MRI apparatus 20 includes a cylinder-shaped static magnetic field magnet 22 for generating a static magnetic field, a cylinder-shaped shim coil 24 coaxially-arranged inside the static magnetic field magnet 22, a gradient magnetic field coil unit 26, RF coils 28, a control system 30, and a bed 32 for placing an object (e.g. a patient) P on it.

Here, as one example, an X axis, a Y axis and a Z axis of an apparatus coordinate system (a device coordinate system) are defined as follows.

Firstly, The X axis, the Y axis and the Z axis are perpendicular to each other.

Secondly, the direction of an axis of the static magnetic field magnet 22 and the shim coil 24 is aligned with the direction which is perpendicular to the vertical direction, and the direction of the axis of the static magnetic field magnet 22 and the shim coil 24 is defined as the Z axis direction.

Thirdly, it is assumed that the vertical direction is the same as the Y axis direction.

Fourthly, the bed 32 is disposed in such a position that the direction of "the normal line of the table plane thereof on which an object is put" is the same as the Y axis direction.

The control system 30 includes a static magnetic field power supply 40, a shim coil power supply 42, a gradient magnetic field power supply 44, an RF transmitter 46, an RF receiver 48, a cooling control device 50, a sequence controller 56 and a computer 58.

The gradient magnetic field power supply 44 includes an X-axis gradient magnetic field power supply 44x, a Y-axis gradient magnetic field power supply 44y and a Z-axis gradient magnetic field power supply 44z.

The computer 58 includes an operation device 60, an input device 62, a display device 64 and a storage device 66.

The static magnetic field magnet 22 is electrically connected to the static magnetic field power supply 40 and generates a static magnetic field in an imaging space by using electric current supplied from the static magnetic field power supply 40.

The shim coil 24 is electrically connected to the shim coil power supply 42 and uniforms the static magnetic field with the electric current supplied from the shim coil power supply 42.

The static magnetic field magnet 22 includes a superconductivity coil in many cases. The static magnetic field magnet 22 gets electric current from the static magnetic field power supply 40 at excitation. However, once excitation has been made, the static magnetic field magnet 22 is usually isolated from the static magnetic field power supply 40. The static magnetic field magnet 22 may include a permanent magnet which makes the static magnetic field power supply 40 unnecessary.

The gradient magnetic field coil unit 26 includes an X-axis gradient coil 26*mx* (i.e. X-axis gradient magnetic field coil 26*mx*), a Y-axis gradient coil 26*my* (i.e. Y-axis gradient magnetic field coil 26*my*) and a Z-axis gradient coil 26*mz* (i.e. Z-axis gradient magnetic field coil 26*mz*).

Each of the X-axis gradient coil 26*mx*, the Y-axis gradient coil 26*my* and the Z-axis gradient coil 26*mz* is cylinder-shaped and arranged inside the static magnetic field magnet 22 (their structure will be explained later with FIG. 2 and FIG. 3).

The X-axis gradient coil 26*mx*, the Y-axis gradient coil 26*my* and the Z-axis gradient coil 26*mz* are electrically connected to the X-axis gradient magnetic field power supply 44x, the Y-axis gradient magnetic field power supply 44y and the Z-axis gradient magnetic field power supply 44z of the gradient magnetic field power supply 44 respectively.

The X-axis gradient magnetic field power supply 44x, the Y-axis gradient magnetic field power supply 44y and the Z-axis gradient magnetic field power supply 44z supply electric current to the X-axis gradient coil 26*mx*, the Y-axis gradient coil 26*my* and the Z-axis gradient coil 26*mz* respectively so as to generate a gradient magnetic field Gx in the X-axis direction, a gradient magnetic field Gy in the Y-axis direction and a gradient magnetic field Gz in the Z-axis direction in the imaging space.

That is, directions of a gradient magnetic field Gss in a slice selection direction, a gradient magnetic field Gpe in a phase encoding direction and a gradient magnetic field Gro in a readout (frequency encoding) direction can be arbitrarily set as logical axes, by combining gradient magnetic fields Gx, Gy and Gz in the X-axis, Y-axis and Z-axis directions as three physical axes.

The gradient magnetic fields Gss, Gpe and Gro in the slice selection direction, the phase encoding direction and the readout direction are superimposed on the static magnetic field.

The RF transmitter 46 generates RF pulses (RF current pulse) of the Larmor frequency for causing nuclear magnetic resonance in accordance with control information provided from the sequence controller 56, and outputs the generated RF pulses to the transmission Rf coil 28

The RF coils 28 include a WBC (whole body coil) built in the gantry for transmission and reception of RF pulses and local coils arranged around the bed 32 or the object P for reception of RF pulses.

The transmission RF coil 28 transmits an RF pulse given from the RF transmitter 46 to the object P. The reception RF coil 28 receives an MR signal generated due to excited nuclear spin inside the object P by the RF pulse and this MR signal is detected by the RF receiver 48.

The RF receiver 48 generates raw data which are digitized complex number data obtained by performing A/D (analogue to digital) conversion after performing predetermined signal processing such as preamplification, phase detection, low-frequency amplification and filtering to the detected MR signal. The RF receiver 48 inputs the generated raw data to the sequence controller 56.

The cooling control device 50 circulates a coolant, such as water, in a cooling pipe 76 (see FIG. 3) described later under the control of a sequence controller 56, thereby suppressing heat generation of a gradient magnetic field coil unit 26.

The operation device 60 performs system control of the MRI apparatus 20 in imaging operation, and its function will be explained later with FIG. 4.

The sequence controller 56 storages control information needed in order to make the gradient magnetic field power supply 44, the RF transmitter 46 and the RF receiver 48 drive. The aforementioned control information includes, for example, sequence information describing operation control information such as intensity, impression period and impression timing of the pulse electric current which should be impressed to the gradient magnetic field power supply 44.

The sequence controller 56 generates the gradient magnetic fields Gx, Gy and Gz in the X-axis, Y-axis and Z-axis directions and RF pulses by driving the gradient magnetic field power supply 44, the RF transmitter 46 and the RF receiver 48 according to a predetermined sequence stored. Additionally, the sequence controller 56 receives raw data of an MR signal inputted from the RF receiver 48, and input the raw data to the operation device 60.

Figure 2:
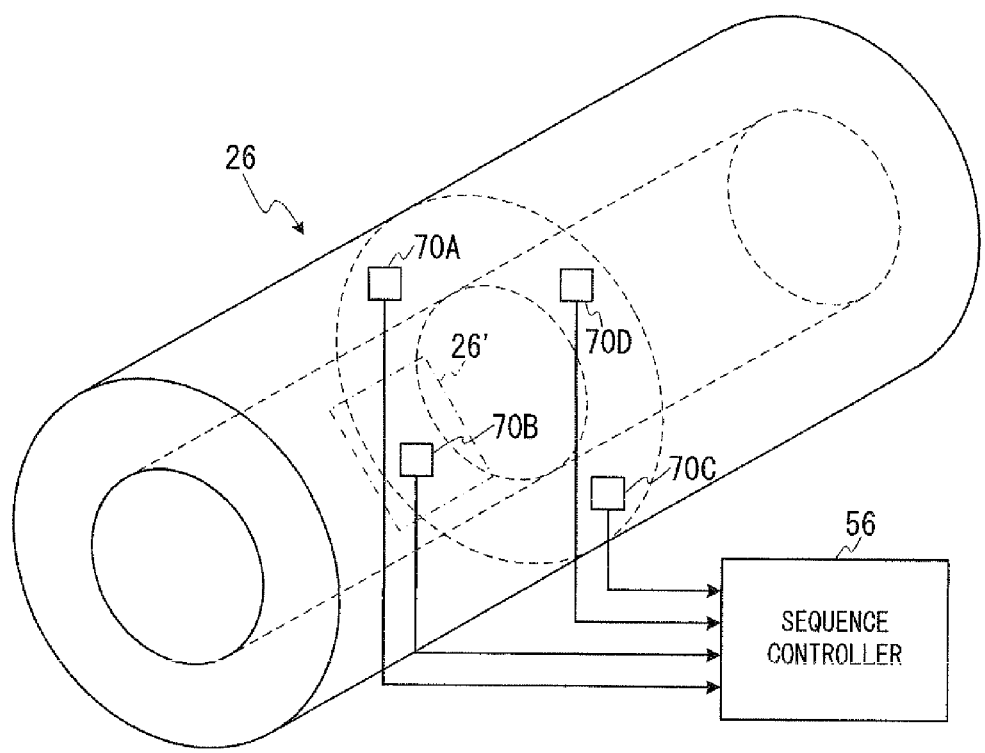
FIG. 2 is a schematic perspective view showing an example of arrangement of temperature sensors in a gradient magnetic field coil unit.

FIG. 2 is a schematic perspective view showing an example of arrangement of temperature sensors in the gradient magnetic field coil unit 26. Four temperature sensors 70A, 70B, 70C, and 70D are arranged at regular intervals along a cylindrical static magnetic field magnet 22 in an annular cross section thereof in an X-Y plane in an apparatus coordinate system including a point that constitutes a magnetic field center during imaging. The temperature sensors 70A to 70D input detected temperatures to the sequence controller 56. The arrangement and the number of the temperature sensors shown in FIG. 2 are only an example, and the arrangement and the number of temperature sensors are not limited to those in the example described above.

Figure 3:
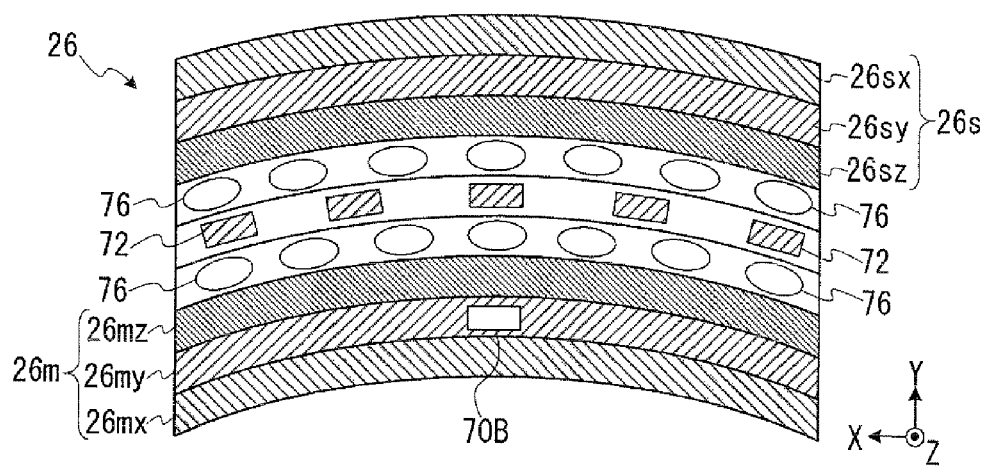
FIG. 3 is a schematic cross-sectional view of the gradient magnetic field coil unit shown in FIG. 2.

FIG. 3 is a schematic cross-sectional view of the gradient magnetic field coil unit 26 shown in FIG. 2 and shows a cross section of a region defined by an alternate long and short dash line 26' in FIG. 2. As shown in FIG. 3, the gradient magnetic field coil unit 26 has a multilayer structure incorporating an active shield. More specifically, the gradient magnetic field coil unit 26 has a layer of a main coil 26m, a layer of a shield coil 26s, and an insertion layer including a plurality of shim trays 72 and embedded layers including a plurality of cooling pipes 76 interposed between the layer of the main coil 26m and the layer of the shield coil 26s. In FIG. 3, the shim tray 72 is shown as a shaded rectangular region, and the cooling pipe 76 is shown as a white elliptical region.

The main coil 26m includes the X-axis gradient coil 26mx, the Y-axis gradient coil 26my, and the Z-axis gradient coil 26mz, which produce the gradient magnetic fields Gx, Gy, and Gz in an imaging region, respectively.

The shield coil 26s includes an X-axis shield coil 26sx, a Y-axis shield coil 26sy, and a Z-axis shield coil 26sz, which produce a magnetic field when a current is supplied thereto from a gradient magnetic field power supply 44.

Specifically, the X-axis shield coil 26sx, the Y-axis shield coil 26sy, and the Z-axis shield coil 26sz produce magnetic fields in a region outside the main coil 26m.

The three magnetic fields respectively produced by X-axis shield coil 26sx, the Y-axis shield coil 26sy, and the Z-axis shield coil 26sz correspond to the X-axis gradient coil 26mx, the Y-axis gradient coil 26my and the Z-axis gradient coil 26mz respectively, and shield the gradient magnetic fields Gx, Gy and Gz produced by the main coil 26m respectively.

A plurality of shim trays 72 are disposed at substantially regular intervals between the embedded layer of cooling pipes 76 closer to the main coil 26m and the embedded layer of cooling pipes 76 closer to the shield coil 26s. Since the coolant is circulated in the cooling pipes 76 by the cooling control device 50, heat generated by the main coil 26m and the shield coil 26s is less likely to transmit to the shim trays 72. The shim trays 72 are, for example, made of a nonmagnetic and nonconductive resin and substantially rod-shaped and extend in the Z-axis direction. The shim tray 72 contains a predetermined number of iron shims (not shown).

In the arrangement shown in FIG. 3, the temperature sensors 70A to 70D detect the temperature of the Y-axis gradient coil 26my. However, this is only an example. In an alternative arrangement, more temperature sensors may be used to separately detect the temperature of the X-axis gradient coil 26mx, the Y-axis gradient coil 26my, the X-axis shield coil 26sx, the Y-axis shield coil 26sy, and the Z-axis shield coil 26sz respectively. As a further alternative, the temperature sensors 70A to 70D may detect the temperature of the shim trays 72. That is, any arrangement is possible as far as the temperature of the gradient magnetic field coil unit 26 can be detected.

Therefore, although an arrangement for detecting the temperature of the cooling water in the cooling pipes 76 is possible, an arrangement for detecting the temperature of a region other than the cooling pipes 76 and their surroundings in the gradient magnetic field coil unit 26 is more preferable. This is because the cooling pipes 76 and their surroundings are the coolest part of the gradient magnetic field coil unit 26, since the coolant for preventing the rise of the temperature of the gradient magnetic field coil unit 26 is flowing in the cooling pipes 76. In other words, an arrangement that directly and accurately detects the temperature of an element that is directly involved with the intensity of the magnetic field in the imaging region is preferable. In this respect, detecting the temperature of the shim trays 72 containing the iron shims or the main coil 26m is superior to detecting the temperature of the cooling pipes 76 and their surroundings.

The temperature sensors 70A to 70D may be infrared radiation thermometers, or thermistors or thermocouples that substantially directly measure the temperature of the main coil 26m. The infrared radiation thermometer is capable of measuring the temperature of an object in a noncontact manner and therefore is advantageous in that it takes a shorter time to measure temperature than a measurement method that requires that the temperatures of the temperature sensor and the object have to become equal by heat transfer.

Figure 4:
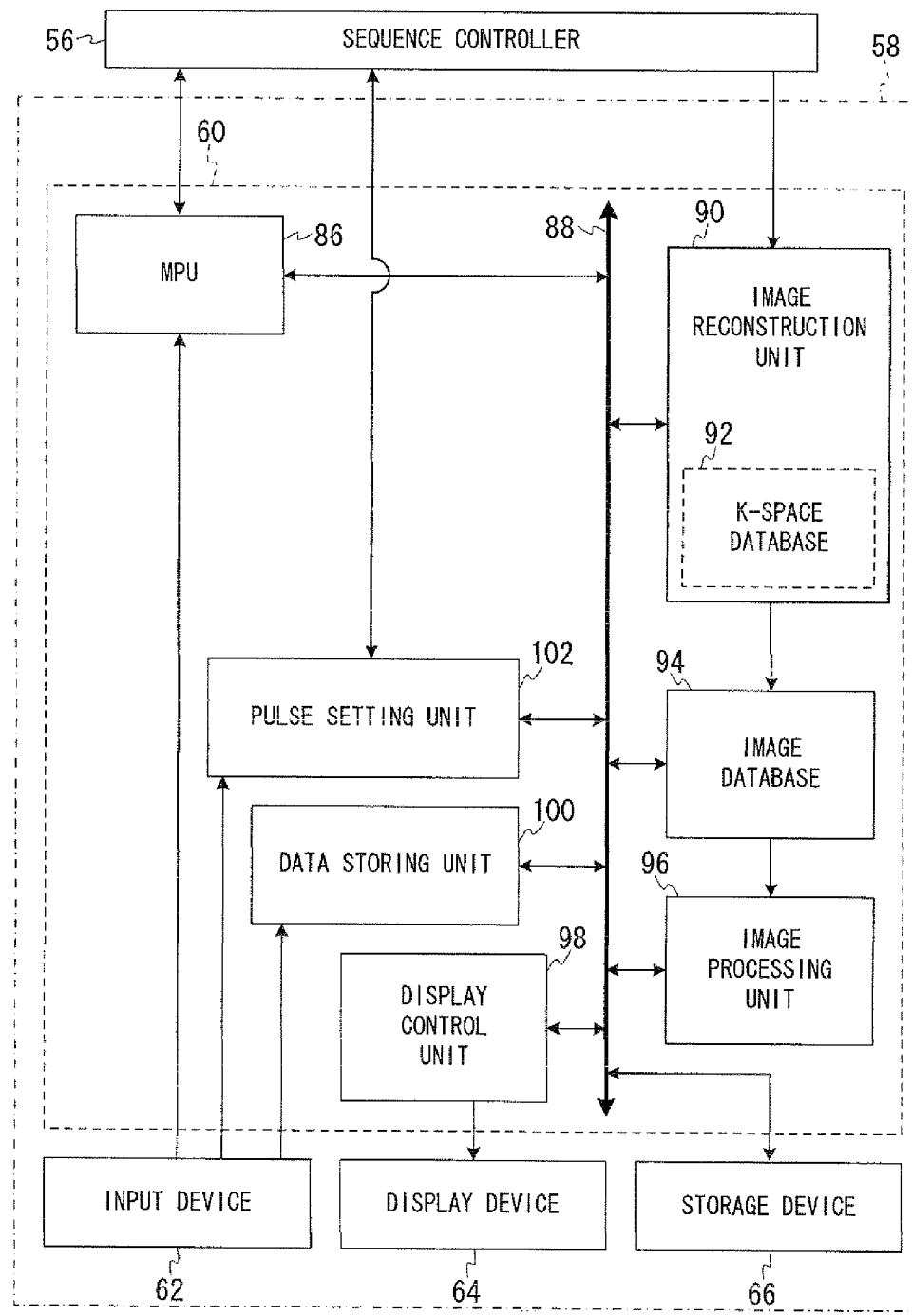
FIG. 4 is a functional block diagram of the computer 58 shown in FIG. 1.

FIG. 4 is a functional block diagram of the computer 58 shown in FIG. 1.

The operation device 60 of the computer 58 includes an MPU (Micro Processor Unit) 86, a system bus 88, an image reconstruction unit 90, an image database 94, an image processing unit 96, an display controlling unit 98, a data storing unit 100, and a pulse setting unit 102.

The MPU 86 performs system control of the MRI apparatus 20 in setting of imaging conditions, imaging operation and image display after imaging through interconnection such as the system bus 88.

Additionally, the MPU 86 functions as imaging conditions setting unit, sets imaging conditions including a pulse sequence such as FSE (Fast Spin Echo) based on command information from the input device 62, and inputs the set imaging conditions into the sequence controller 56. In order to achieve it, the MPU 86 controls the display controlling unit 98 and displays information for setting imaging conditions on the display device 64.

The input device 62 provides a user with a function to set imaging conditions and image processing conditions.

The image reconstruction unit 90 includes a k-space database 92 inside. The image reconstruction unit 90 arranges raw data of MR signals inputted from the sequence controller 56 in the k-space formed in the k-space database 92 as k-space data. The image reconstruction unit 90 generates image data of each slice of the object P by performing image reconstruction processing including such as 2-dimensional Fourier transformation. The image reconstruction unit 90 stores the generated image data in the image database 94.

The image processing unit 96 takes in the image data from the image database 94, performs predetermined image processing on them, and stores the image data after the image processing in the storage device 66 as image data for display.

The storage device 66 stores the image data for display after adding "accompanying information such as imaging conditions used for generating the image data for display and information of the object P (patient information)" to the image data for display.

The display controlling unit 98 displays a screen for setting imaging conditions and an image indicated by generated image data through imaging on the display device 64 under control of the MPU 86.

The data storing unit 100 stores shift data that indicate a relationship between the variation of the temperature of the gradient magnetic field coil unit 26 and the shift of the center frequency of the magnetic resonance of hydrogen atoms. The shift data are generated and recorded in a temperature coefficient acquisition sequence (described later) performed during installation of an MRI apparatus 20, for example. The temperature coefficient acquisition sequence is not necessarily performed as a part of an installation adjustment during installation, but can also be performed to calibrate the shift data during a regular inspection, for example.

The pulse setting unit 102 acquires the temperatures detected by the temperature sensors 70A to 70D via the sequence controller 56, calculates the temperature variation of the gradient magnetic field coil unit 26, and sets the center frequency of an RF pulse based on the shift data. The RF pulse referred to herein may be a fat suppression prepulse, a region-selective pre-saturation pulse, or a 90° excitation pulse or refocusing pulse for data collection.

Description of Operation According to an Embodiment

In the temperature coefficient acquisition sequence, which is one characteristic of this embodiment, a pulse sequence that involves a temperature rise is performed, and the temperatures detected by the temperature sensors 70A to 70D and the center frequency of the magnetic resonance of hydrogen atoms are measured over time. Then, the shift of the center frequency in response to the variation of the temperature in the gradient magnetic field coil unit 26 is calculated based on the measurement result, and the shift is recorded in the data storing unit 100 as shift data. Even with the same pulse sequence, the temperature rises in different, specific ways depending on the individual MRI apparatus 20. Therefore, the temperature coefficient acquisition sequence is preferably performed for each MRI apparatus when the MRI apparatus is installed, for example.

An example of the temperature coefficient acquisition sequence is a pulse sequence in which the temperature of the gradient magnetic field coil unit 26 rises in approximate proportion to the length of the time elapsed. With this pulse sequence, the temperatures detected by the temperature sensors 70A to 70D are acquired as chronological data. At the same time, the position of a peak in a frequency spectrum of a magnetic resonance signal is detected by magnetic resonance spectroscopy, for example, thereby acquiring the center frequency of the magnetic resonance of hydrogen atoms in a phantom (such as water) as chronological data. Note that a water content tissue and a fat tissue do not have to be distinguished, because hydrogen atoms in the water content tissue in the human body and hydrogen atoms in the fat tissue in the human body experience approximately equal center frequency shifts in response to a rise of the temperature of the gradient magnetic field coil.

Figure 5A:
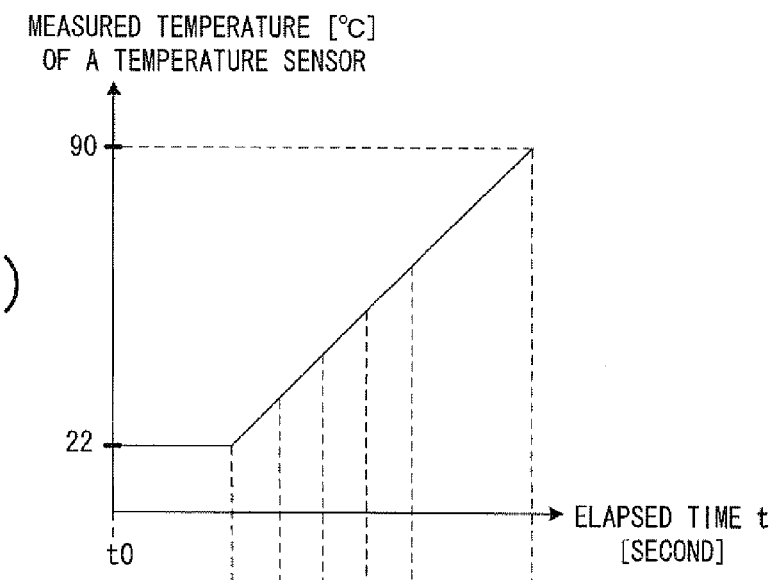
FIG. 5 is an explanatory diagram showing a temporal variation of "the temperature detected by the temperature sensor 70A in a temperature coefficient acquisition sequence" and "the center frequency of the magnetic resonance of hydrogen atoms"
Figure 5B:
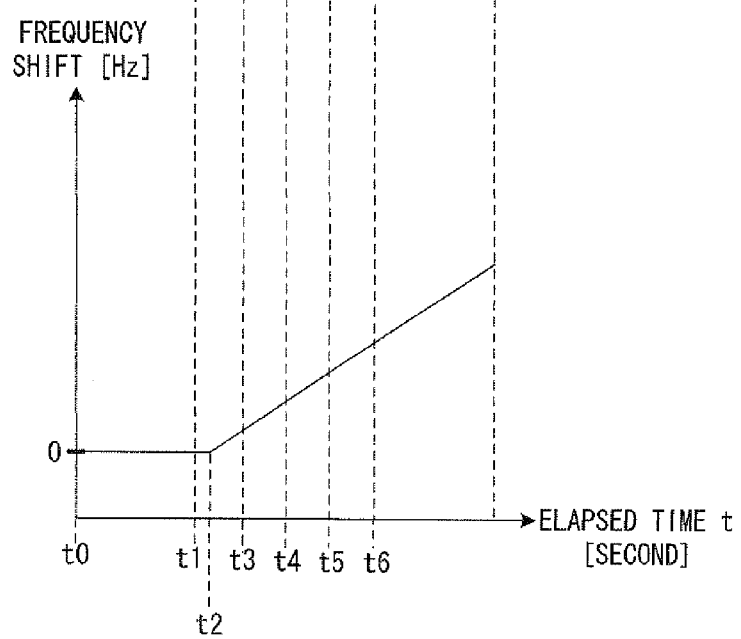

FIG. 5(A) shows a temporal variation of the temperature detected by the temperature sensor 70A in the temperature coefficient acquisition sequence, and FIG. 5(B) shows a temporal variation of the center frequency of the magnetic resonance of hydrogen atoms in the temperature coefficient acquisition sequence. In both FIGS. 5(A) and 5(B), the abscissa axis indicates the time elapsed from a start time t0 of the temperature coefficient acquisition sequence. The ordinate axis in FIG. 5(A) indicates the temperature (° C.) detected by the temperature sensor 70A, and the ordinate axis in FIG. 5(B) indicates the shift (Hz) of the center frequency of the magnetic resonance of hydrogen atoms.

Considering a coordinate system in which the abscissa axis indicates the temperature and the ordinate axis indicates the magnetic permeability of the iron shim in the shim tray 72, the magnetic permeability approximately linearly varies with temperature within a normal operating temperature range of the MRI apparatus (from 20° C. to 90° C., for example). This embodiment takes advantage of this phenomenon. Specifically, if the magnetic permeability of the iron shim linearly varies as the temperature rises, the intensity (Tesla) of the magnetic field in the imaging region also linearly varies as the temperature rises, and accordingly, the center frequency of the magnetic resonance of hydrogen atoms in the imaging region also linearly varies as the temperature rises. This is because the Larmor frequency is proportional to the intensity of the applied magnetic field.

There is a slight delay time (time interval) between a time t1 at which the temperature detected by the temperature sensor 70A starts rising and a time t2 at which the center frequency of the magnetic resonance of hydrogen atoms starts shifting. For simplicity of explanation, the delay time is not considered herein. However, the delay time may be considered in preparing the shift data.

Since the sensitivity varies with the individual temperature sensors 70A to 70D, a temperature coefficient, which indicates the shift (Hz) of the center frequency in response to a unit temperature rise (1 Kelvin, that is, 1° C.) of the detected temperature, is determined for each temperature sensor 70A to 70D. Supposing that the temperature rise is denoted by $\Delta Tp$, and the shift of the center frequency corresponding to the temperature rise is denoted by $\Delta Hz$, a temperature coefficient KA of the temperature sensor 70A is determined according to $KA=\Delta Hz/\Delta Tp$. Similarly, a temperature coefficient KB of the temperature sensor 70B, a temperature coefficient KC of the temperature sensor 70C, and a temperature coefficient KD of the temperature sensor 70D are determined as $\Delta Hz/\Delta Tp$.

A first example of the method of determining the temperature coefficients KA to KD is the least square method. Specifically, temperatures detected by the temperature sensor 70A at a plurality of different times after the time t2 (falling within a range of about 20° C. to 90° C., for example) are plotted as chronological data, and the slope of the graph (which corresponds to the graph shown in FIG. 5(A)) is calculated by the least square method. Similarly, shifts of the center frequency at a plurality of different times subsequent to the time t2 are plotted as chronological data, and the slope of the graph (which corresponds to the graph shown in FIG. 5(B)) is calculated by the least square method. Then, the slope of the graph shown in FIG. 5(B) is divided by the slope of the graph shown in FIG. 5(A) to determine the temperature coefficient KA. The temperature coefficients KB, KC, and RD can be calculated in the same way.

A second example of the method of determining the temperature coefficients KA to KD is to use simultaneous equations. Specifically, variations of the temperatures detected by the temperature sensors 70A, 70B, 70C, and 70D are measured at a time t3 subsequent to the time t2. The variations of the temperatures detected by the temperature sensors 70A, 70B, 70C, and 70D are denoted by $\Delta Tp1A$, $\Delta Tp1B$, $\Delta Tp1C$, and $\Delta Tp1D$, respectively. In this example, the differences from the temperatures detected at the start time t0 of the temperature coefficient acquisition sequence are determined as the temperature variations $\Delta Tp1A$ to $\Delta Tp1D$ (in the case of the temperature sensor 70A shown in FIG. 5(A), the temperature variation is obtained by subtracting 22° C. from the measured temperature). Then, based on the result of measurement by magnetic resonance spectroscopy, the shift $\Delta Hz1$ of the center frequency at the time t3 with respect to the shift of the center frequency at the time t0 is determined. Thus, the following formula (1) is obtained.

$$(\Delta Tp1A \times KA + \Delta Tp1B \times KB + \Delta Tp1C \times KC + \Delta Tp1D \times KD) \div 4 = \Delta Hz1 \quad (1)$$

Since the temperature coefficients KA to KD are defined as the shift of the center frequency per unit temperature rise, the formula (1) takes an average of the shifts of the center frequency, which is the product of the temperature coefficient and the temperature variation, among the four temperature sensors 70A to 70D, for example.

Similarly, temperature variations detected by the temperature sensors 70A to 70D as $\Delta Tp2A$ to $\Delta Tp2D$ are measured at a time t4 subsequent to the time t3. Then, supposing that the shift of the center frequency at the time t4 with respect to the shift of the center frequency at the time t0 is denoted by $\Delta Hz2$, the following formula (2) is obtained.

$$(\Delta Tp2A \times KA + \Delta Tp2B \times KB + \Delta Tp2C \times KC + \Delta Tp2D \times KD) \div 4 = \Delta Hz2 \quad (2)$$

By similar measurements at a time t5 subsequent to the time t4 and a time t6 subsequent to the time t5, the following formulas (3) and (4) are obtained.

$$(\Delta Tp3A \times KA + \Delta Tp3B \times KB + \Delta Tp3C \times KC + \Delta Tp3D \times KD) \div 4 = \Delta Hz3 \quad (3)$$

$$(\Delta Tp4A \times KA + \Delta Tp4B \times KB + \Delta Tp4C \times KC + \Delta Tp4D \times KD) \div 4 = \Delta Hz4 \quad (4)$$

Since the formulas (1) to (4) include only four unknown factors KA, KB, KC, and KD, the temperature coefficients KA to KD can be determined by solving the formulas (1) to (4) as simultaneous equations. In the case where the coefficients KA to KD are determined by solving the simultaneous equations in this way, as many measurement data as the temperature sensors are required.

The method of determining the temperature coefficients KA to KD is not limited to the two methods described above, but any other methods can be used. In addition, although the temperature coefficient KA is defined according to $KA = \Delta Hz/\Delta Tp$, the temperature coefficient KA may be the inverse of the value ($\Delta Tp/\Delta Hz$) (the same holds true for KB to KD).

In addition, although the products of the temperature variation $\Delta T$ and the temperature coefficient based on the result of detection by the temperature sensors 70A to 70D are summed and averaged over all the temperature sensors 70A to 70D in this embodiment, this method is only an example, and other methods can be used. For example, many temperature sensors may be provided, and temperatures detected by a plurality of temperature sensors in the vicinity of a region where the temperature is likely to rise may be used.

Figure 6:
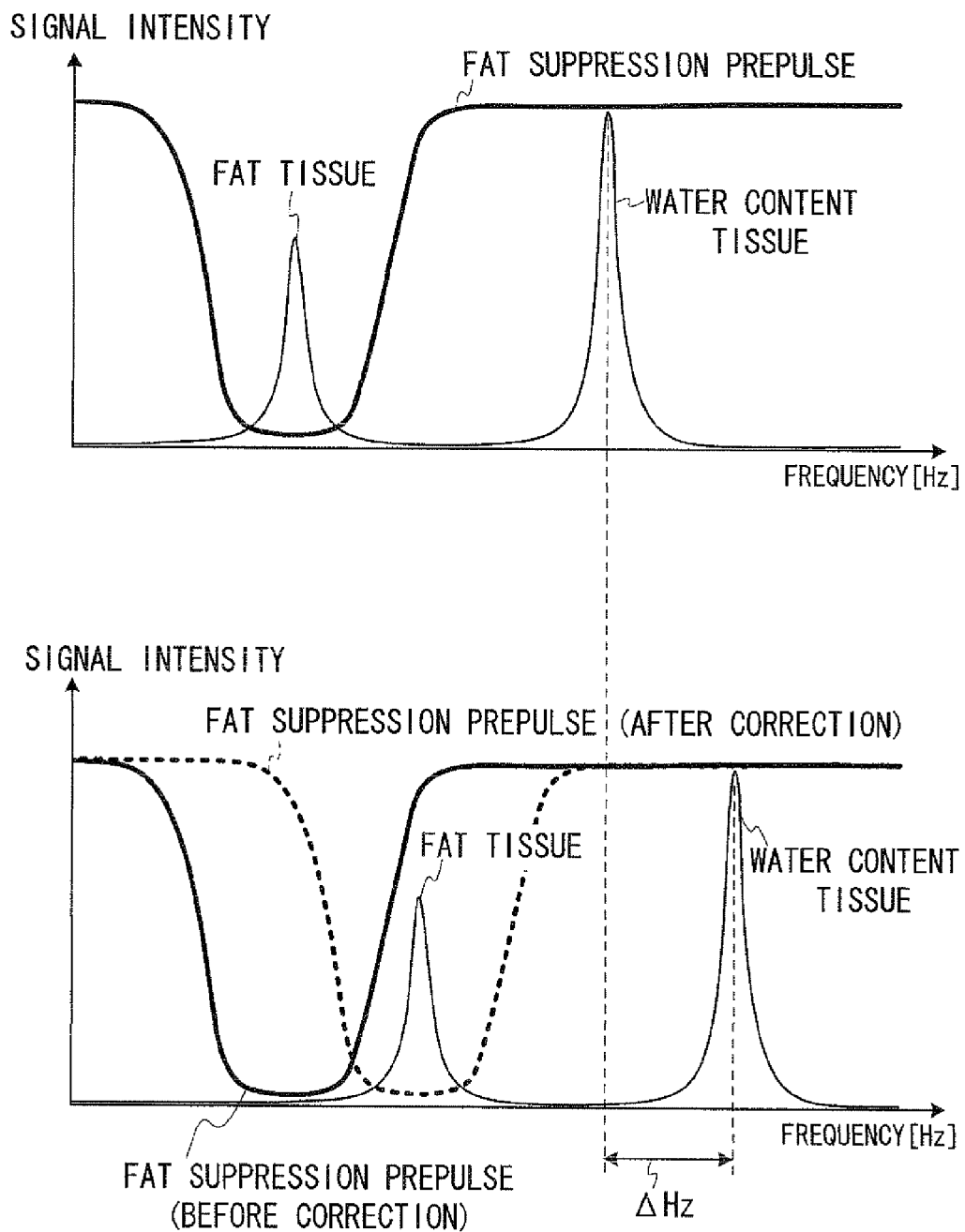
FIG. 6 is a diagram for illustrating the effect of a fat suppression prepulse according to the present embodiment.

FIG. 6 is a diagram for illustrating the effect of a fat suppression prepulse according to this embodiment. In FIG. 6, the abscissa axis indicates the frequency (Hz), and the ordinate axis indicates the signal intensity of an MR signal. The upper part of FIG. 6 shows a frequency spectrum of hydrogen atoms in a fat tissue and hydrogen atoms in a water content tissue and the signal intensity of the fat suppression prepulse superposed on the frequency spectrum, before the temperature of the gradient magnetic field coil unit 26 starts rising. In a prescan, based on the temperature of the gradient magnetic field coil unit 26 at the time when the prescan is performed, for example, the center frequency of the fat suppression prepulse is (provisionally) set to agree with the peak of the signal intensity of hydrogen atoms in the fat tissue at that temperature.

The lower part of FIG. 6 shows a frequency spectrum of hydrogen atoms in the fat tissue and in the water content tissue and the signal intensity of the fat suppression prepulse superposed on the frequency spectrum, after the temperature of the gradient magnetic field coil unit 26 starts rising. Once the center frequency of the fat suppression prepulse is set, if the temperature of the gradient magnetic field coil unit 26 rises, the peak of the signal intensity of hydrogen atoms in the fat tissue and the water content tissue shifts by $\Delta Hz$ as shown in the lower part of FIG. 6. If this occurs, the center frequency of the fat suppression prepulse set in the prescan shown by the solid line deviates from the peak of the signal intensity of hydrogen atoms in the fat tissue, and thus, the effect of fat suppression is degraded.

To the contrary, according to this embodiment, after the center frequency of the fat suppression prepulse is provisionally set in the prescan, the temperature of the gradient magnetic field coil unit 26 is measured before a main scan. Then, based on the temperature variation and the shift data, the center frequency of the fat suppression prepulse is corrected before the main scan as shown by the dashed line in the lower part of FIG. 6. In this way, according to this embodiment, regardless of the temperature rise in the gradient magnetic field coil unit 26, the center frequency of the fat suppression prepulse is made to agree with the peak of the signal intensity of hydrogen atoms in the fat tissue, thereby ensuring the effect of the fat suppression.

Figure 7:
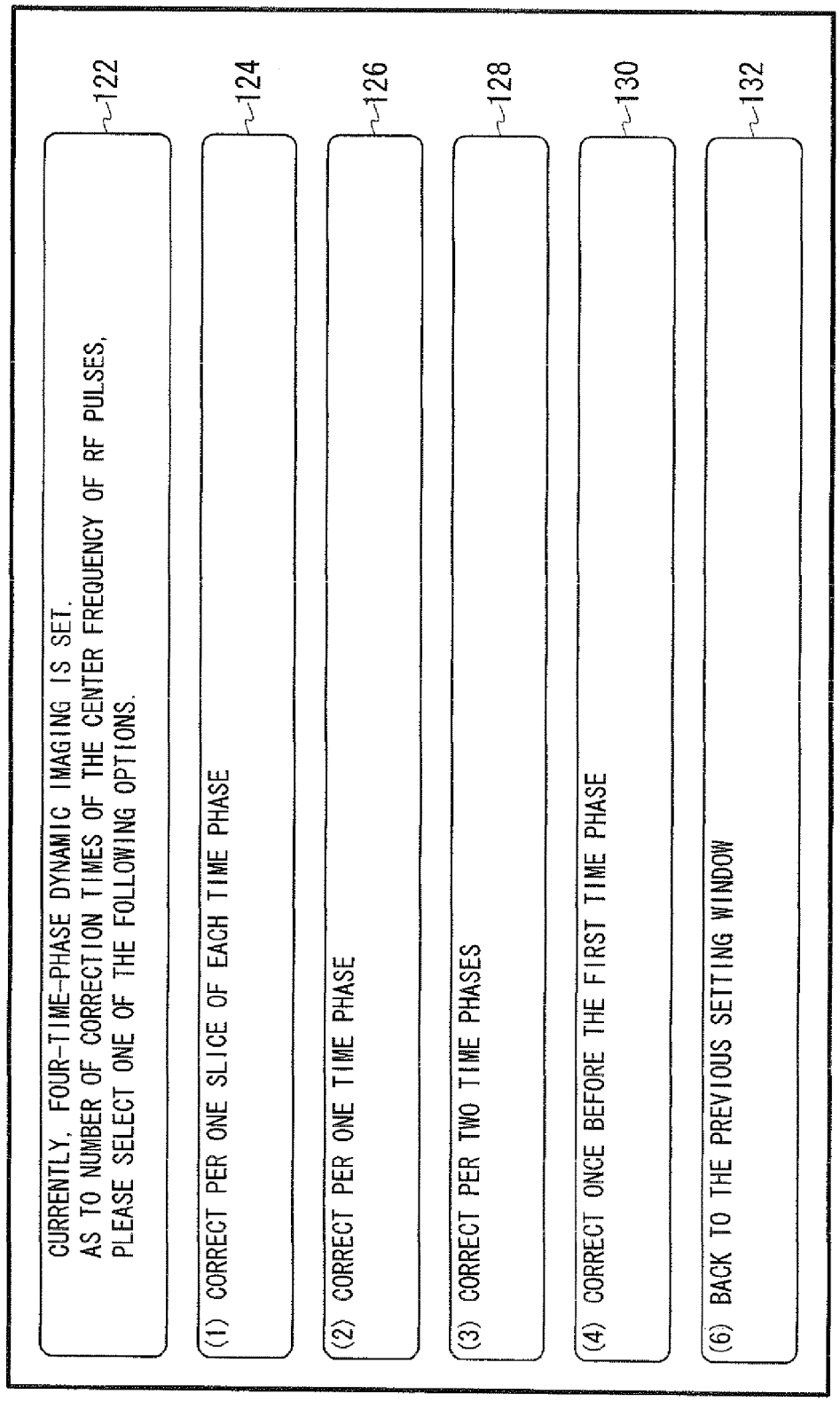
FIG. 7 is a schematic diagram showing an example of a screen displayed on a monitor of a display device 64, when the timing of correcting the center frequency of an RF pulse is inputted and set.

FIG. 7 is a schematic diagram showing an example of a screen displayed on a monitor of a display device 64, when the timing of correcting the center frequency of the RF pulse is inputted and set. As shown in FIG. 7, in a frame shown by the bold line, which indicates the outer edge of the screen, a display window 122 in which a setting status is described and display regions 124, 126, 128, 130, and 132 for selection input are displayed. In this example, as can be seen from the description in the display window 122, a four-time-phase dynamic imaging is already set.

A user can select to correct the center frequency of the RF pulse for each slice in each time phase by inputting "1" via an input device 62 (the value "1" corresponds to the display region 124).

A user can select to correct the center frequency of the RF pulse for each time phase by inputting "2" via an input device 62 (the value "2" corresponds to the display region 126).

A user can select to correct the center frequency of the RF pulse every two time phases by inputting "3" via an input device 62 (the value "3" corresponds to the display region 128).

A user can select to correct the center frequency of the RF pulse only once just before the first time phase by inputting "4" via an input device 62 (the value "4" corresponds to the display region 130).

The user can select to return to the previous setting screen by inputting "6" via the input device 62 (the value "6" corresponds to the display region 132).

The input device 62 and the display device 64 may be integrated to support touch-screen input.

Figure 8:
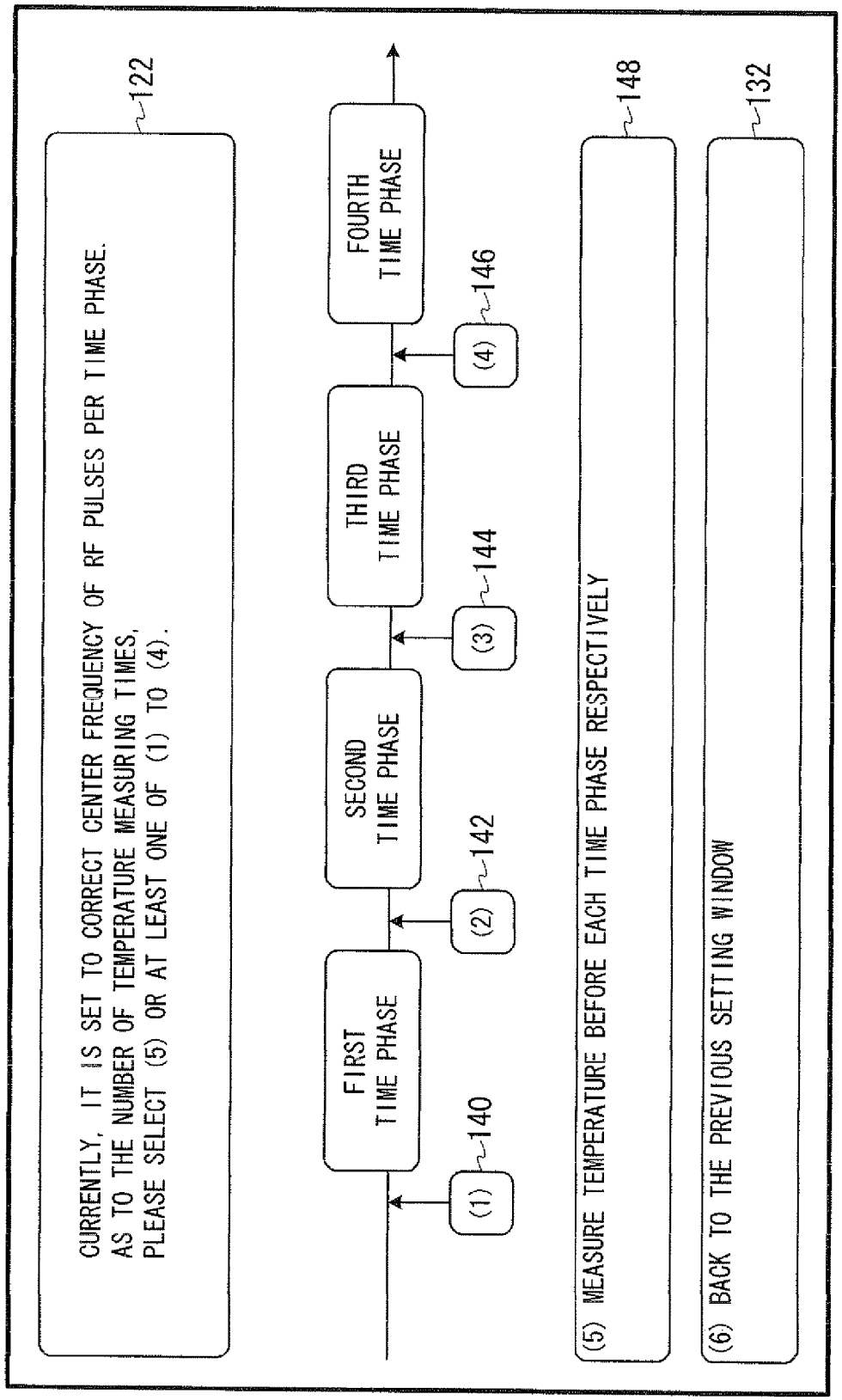
FIG. 8 is a schematic diagram showing an example of a screen displayed on the monitor of the display device 64 subsequently to the screen shown in FIG. 7, when the timing of correcting the center frequency of the RF pulse is inputted and set.

If "2" is inputted and selected on the screen shown in FIG. 7, a screen display such as one shown in FIG. 8 appears, on which the user can input and set the timing of temperature measurement.

FIG. 8 is a schematic diagram showing an example of a screen displayed on the monitor of the display device 64 subsequently to the screen shown in FIG. 7, when the timing of correcting the center frequency of the RF pulse is inputted and set.

The user can select to perform temperature measurement for center frequency correction before start of each imaging in each time phase by inputting "5" via the input device 62 (the value "5" corresponds to a display region 148), for example.

The user can select to perform temperature measurement for center frequency correction before start of imaging in the first time phase by inputting "1" via the input device 62 (the value "1" corresponds to a display region 140), for example. Similarly, the timing of correcting the center frequency can be set by inputting "2" (which corresponds to a display region 142), "3" (which corresponds to a display region 144), and "4" (which corresponds to a display region 146) via the input device 62.

Alternatively, the user can select to perform temperature measurement for center frequency correction at three times, that is, before start of imaging in the first time phase, before start of imaging in the second time phase, and before start of imaging in the fourth time phase, by inputting only "1", "2", and "4" via the input device 62, for example. In this case, after the imaging in the second time phase is finished, temperature measurement is not performed before start of imaging in the third time phase. The same holds true for other combinations of two or three of the input values "1", "2", "3", and "4". That is, if the user inputs and selects only one, two, or three of the values "1", "2", "3", and "4", it means that the user selects not to perform temperature measurement at the remaining timings.

In other words, the input device 62 is configured to be capable of selecting both the timings at which temperature measurement is not performed and the timings at which temperature measurement is performed from among a plurality of timing candidates for temperature measurement displayed on the display device 64.

Figure 9:
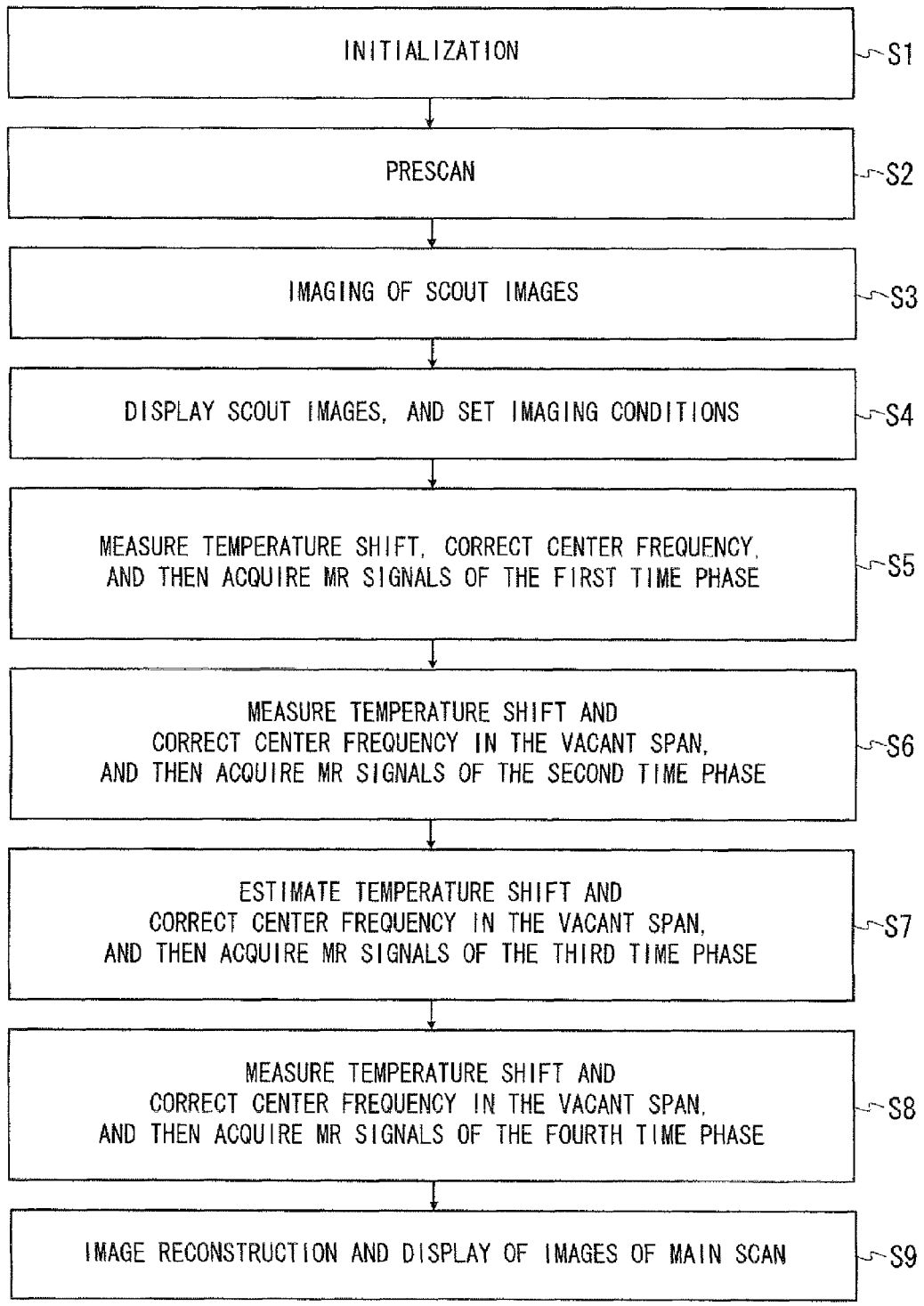
FIG. 9 is a flowchart illustrating a flow of a process performed by the MRI apparatus of the present embodiment.

FIG. 9 is a flowchart showing a flow of a four-time-phase dynamic imaging operation performed by the MRI apparatus 20, for example. In the following, according to the step numbers in the flowchart shown in FIG. 9, an operation of the MRI apparatus 20 will be described by referring to the aforementioned FIGS. 1 to 8 as required.

[Step S1] The MPU 86 (see FIG. 4) initializes the MRI apparatus 20 based on information inputted via the input device 62, for example. In the initialization, information on the posture of the object P with respect to the X axis, the Y axis, and the Z axis of the apparatus coordinate system and information on the imaging region are set, for example. In this embodiment, a four-time-phase dynamic imaging is set in step S1, for example.

In each time phase, for example, MR signals for 50 slices of images are collected under the same imaging conditions except for the center frequency of the RF pulse. At the same time, the length of the vacant span between time phases of dynamic imaging is also set. During the vacant span, no pulses are transmitted, and no signals are received from the object P. Note that the number of time phases may not be four, and the number of slices in each time phase can be arbitrarily changed.

In response to an instruction from the MPU 86, a display control unit 98 displays the imaging time calculated from the set imaging conditions and the input screen for selecting the frequency of correction of the center frequency of the RF pulse during imaging on the monitor of the display device 64 (see FIGS. 7 and 8). In this example, since the four-time-phase dynamic imaging is performed, the user can select to perform the correction only once immediately before the first time phase, to perform the correction every two time phases, to perform the correction for each time phase, or to perform the correction for each slice in each time phase, for example. In this example, it is assumed that the correction is performed for each time phase.

The display control unit 98 also displays the input screen for selecting the timing of measuring the temperature of the gradient magnetic field coil unit 26 on the monitor of the display device 64 in response to an instruction from the MPU 86 (see FIG. 8). In this example, since the user has selected to perform the correction of the center frequency of the RF pulse for each time phase as described above, the following four timings are displayed as choices.

A first choice is a timing after an operator finally determines the imaging conditions based on scout images displayed in Step S4 described later and before start of a pulse sequence of a first time phase of the dynamic imaging (this timing corresponds to the display region 140 in FIG. 8 and will be referred to as the first timing hereinafter).

A second choice is a timing during the vacant span after completion of the pulse sequence of the first time phase of the dynamic imaging and before start of the pulse sequence of the second time phase (this timing corresponds to the display region 142 in FIG. 8 and will be referred to as the second timing hereinafter).

A third choice is a timing during the vacant span after completion of the pulse sequence of the second time phase of the dynamic imaging and before start of the pulse sequence of the third time phase (this timing corresponds to the display region 144 in FIG. 8 and will be referred to as the third timing hereinafter).

A fourth choice is the timing during the vacant span after completion of the pulse sequence of the third time phase of the dynamic imaging and before start of the pulse sequence of the fourth time phase (this timing corresponds to the display region 146 in FIG. 8 and will be referred to as a fourth timing hereinafter).

In this example, with the input device 62, the first, the second, and the fourth timing are selected as on-timings at which temperature measurement is performed, and the third timing is selected to not perform temperature measurement.

However, this is only an example. For example, temperature detection may be performed in all the vacant spans (the first to fourth timings in this example) during the dynamic imaging, and the center frequency of the RF pulse may be corrected in all the vacant spans. Alternatively, temperature detection may be performed between every adjacent slices (that is, between collection of an MR signal for each slice and collection of an MR signal for the next slice), and the center frequency of the RF pulse may be corrected between every adjacent slice.

The cooling control device 50 circulates the coolant in the cooling pipes 76 under the control of the sequence controller 56, thereby adjusting the temperature of the gradient magnetic field coil unit 26 to be 22° C. shown in FIG. 5(A), for example. At a timing when the temperature of the gradient magnetic field coil unit 26 becomes substantially stable at (or converges to) an initial value, for example, immediately before start of prescan in the next step S2, the temperature sensors 70A to 70D (see FIGS. 2 and 3) each detect the temperature in the gradient magnetic field coil unit 26 as an initial temperature. The initial temperatures detected by the temperature sensors 70A to 70D are inputted to the pulse setting unit 102 via the sequence controller 56.

The timing of measurement of the initial temperature may not be immediately before start of the prescan described above but may be during the prescan or immediately after completion of the prescan.

When the temperature sensors tend to be affected by noise of the gradient magnetic fields or the RF pulse, the effect of noise can be advantageously avoided by performing temperature measurement immediately before start of the prescan or immediately after completion of the prescan.

When the temperature sensors do not tend to be affected by noise of the gradient magnetic fields or the RF pulse, temperature can be more accurately detected by performing temperature measurement during the prescan.

[Step 2] The MRI apparatus 20 performs the prescan to make calculations on the imaging conditions. For example, the MRI apparatus 20 calculates the power required for the RF pulse to rotate a longitudinal magnetization component of a nuclear spin by 90° (90° condition) or the provisional center frequency of RF pulses such as the fat suppression prepulse and the excitation pulse.

The provisional center frequency of the RF pulses is set by the pulse setting unit 102 so as to agree with the center frequency of the magnetic resonance of hydrogen atoms at the initial temperature, for example. Alternatively, the temperature sensors 70A to 70D may detect the temperature of the gradient magnetic field coil unit 26 during the prescan, and the provisional center frequency of the RF pulses may be set to agree with the center frequency of the magnetic resonance of hydrogen atoms at the detected temperature.

[Step S3] The scout images are generated. More specifically, the MRI apparatus 20 transmits an RF pulse for image data collection and receives an MR signal from the object P at the RF receiver 48. The sequence controller 56 inputs raw data of the MR signal to the image reconstruction unit 90, and the image reconstruction unit 90 performs a predetermined processing on the raw data to generate image data of the scout images and inputs the image data to the image database 94. The image processing unit 96 performs a predetermined image processing on the image data inputted to the image database 94, and a storage device 66 stores the image data of the scout images having been subjected to the image processing.

[Step S4] The display control unit 98 displays the scout images on the monitor of the display device 64 in response to an instruction from the MPU 86. Based on the displayed images, imaging conditions such as the imaging region are set.

[Step S5] Then, imaging of a diagnostic image (the so-called main scan) is performed. First, the temperature sensors 70A to 70D each detect the temperature in the gradient magnetic field coil unit 26 as the temperature at the first timing, and input the temperature to the pulse setting unit 102 via the sequence controller 56.

Then, the pulse setting unit 102 reads in the shift data described earlier from the data storing unit 100. The pulse setting unit 102 calculates the difference $\Delta TpA\_T1$ between" the temperature detected by the temperature sensor 70A as the initial temperature" and "the temperature detected as the temperature at the first timing". Similarly, the pulse setting unit 102 calculates the differences $\Delta TpB\_T1$, $\Delta TpC\_T1$, and $\Delta TpD\_T1$ between the temperatures detected by the temperature sensors 70B to 70D as the initial temperature and the temperature detected as the temperature at the first timing.

Then, the pulse setting unit 102 calculates an average value of the four values $\Delta TpA\_T1$, $\Delta TpB\_T1$, $\Delta TpC\_T1$, and $\Delta TpD\_T1$, and determines the shift of the center frequency of the magnetic resonance of hydrogen atoms from this average value and the shift data. Then, the pulse setting unit 102 corrects the center frequency of the RF pulse, such as the fat suppression prepulse and the excitation pulse, provisionally set in the prescan by shifting the center frequency by the determined shift.

The sequence controller 56 controls each unit in the MRI apparatus 20 according to an instruction from the MPU 86 and transmits an RF pulse having the center frequency corrected by the pulse setting unit 102 to make the MRI apparatus 20 acquire (collect) MR signals for each slice in the first time phase of the dynamic imaging.

More specifically, a static magnetic field is formed in the imaging space by the static magnetic field magnet 22 excited by the static magnetic field power supply 40. In addition, electric current is supplied from the shim coil power supply 42 to the shim coil 24, thereby the static magnetic field formed in the imaging space is uniformed.

Then, when the MPU 86 receives a command of start of imaging from the input device 62, the MPU 86 inputs imaging conditions including a pulse sequence into the sequence controller 56. Then, the sequence controller 56 drives the gradient magnetic field power supply 44, the RF transmitter 46 and the RF receiver 48 according to the inputted pulse sequence, thereby gradient magnetic fields are formed in the imaging region, where the object P is set, and RF signals are generated from the RF coil 28.

Then, MR signals generated by nuclear magnetic resonance inside the object P are received by the RF coil 28 and transmitted to the RF receiver 48. The RF receiver 48 performs predetermined signal processing on the detected MR signals and then performs A/D conversion on the MR signals to generate raw data, which are digital data of the MR signals. The RF receiver 48 inputs the generated raw data to the sequence controller 56.

The sequence controller 56 inputs the raw data to the image reconstruction unit 90.

The image reconstruction unit 90 arranges the raw data in the k-space formed in the k-space database 92 as k-space data, thereby k-space data are stored.

The MR signal collection and the data recording processing for one slice are performed as many times as the number of slices.

[Step S6] Data acquisition for the second time phase is performed in the same way as the data acquisition for the first time phase following a predetermined vacant span after the data acquisition for the first time phase of dynamic imaging is completed. First, the temperature sensors 70A to 70D each detect the temperature in the gradient magnetic field coil unit 26 as the temperature at the second timing, and input the temperature to the pulse setting unit 102 via the sequence controller 56.

Then, in the similar way to Step S5, the pulse setting unit 202 calculates the differences between the temperatures detected by the temperature sensors 70A to 70D as the initial temperature and the temperature detected as the temperature at the second timing, and calculates an average value of the differences.

The pulse setting unit 102 determines the shift of the center frequency of the magnetic resonance of hydrogen atoms from the average value and the shift data, and corrects the center frequency of the RF pulse so as to agree with the center frequency of the magnetic resonance of hydrogen atoms at the temperature of the gradient magnetic field coil unit 26 at the second timing.

After that, the pulse setting unit 102 transmits the RF pulse having the center frequency corrected again by the pulse setting unit 102 and acquires the MR signal for each slice in the second time phase of dynamic imaging.

[Step S7] Data acquisition for the third time phase is performed following a predetermined vacant span after the data acquisition for the second time phase of the dynamic imaging is completed. At the third timing during the vacant span before start of data acquisition for the third time phase, the temperature sensors 70A to 70D do not perform temperature detection according to the setting inputted in Step S1.

The pulse setting unit 102 calculates an estimation value of the temperature of the gradient magnetic field coil unit 26 at the third timing based on the temperature detected by the temperature sensors 70A to 70D at a timing preceding the third timing. For example, the estimation value is determined based on a plurality of measurement data plotted on a coordinate system in which the abscissa axis indicates the elapsed time (measurement time) and the longitudinal axis indicates the temperature.

More specifically, a straight line is determined that connects a first plot and a second plot. The first plot is determined by the first timing as the measurement time and the average value of the temperatures detected by the temperature sensors 70A to 70D at the first timing. The second plot is determined by the second timing as the measurement time and the average value of the temperatures detected by the temperature sensors 70A to 70D at the second timing.

Then, the estimation value of the temperature in the gradient magnetic field coil unit 26 at the third timing is determined along the straight line.

The method of calculating the estimation temperature value is not limited to the method described above.

For example, the temperature sensors 70A to 70D may detect temperature four or more times at different measurement times during a period after start of the main scan (Step S5) and before the third timing. These temperatures may be plotted on a coordinate system in which the abscissa axis indicates the elapsed time and the ordinate axis indicates the temperature, and the slope of this graph may be determined by the least square method. And then, the estimation value of the temperature at the third timing can be calculated based on the determined slope in the same manner as described above.

Next, the pulse setting unit 102 determines the shift of the center frequency of the magnetic resonance of hydrogen atoms at the third timing from the calculated estimation temperature value and the shift data, and corrects the center frequency of the RF pulse so as to agree with the center frequency of the magnetic resonance of hydrogen atoms at the temperature at the third timing. After that, the RF pulses having the center frequency corrected again by the pulse setting unit 102 are transmitted, and the MR signals for each slice in the third time phase of the dynamic imaging are acquired.

[Step S8] Data acquisition for the fourth time phase is performed in the same way as data acquisition for the first and second time phases following a predetermined vacant span after the data acquisition for the third time phase of the dynamic imaging is completed. That is, the temperature sensors 70A to 70D each detect the temperature in the gradient magnetic field coil unit 26 as the temperature at the fourth timing, and input the temperature to the pulse setting unit 102 via the sequence controller 56.

Then, the pulse setting unit 102 calculates an average value of the differences between the temperatures detected by the temperature sensors 70A to 70D as the initial temperature and the temperature detected as the temperature at the fourth timing, determines the shift of the center frequency of the magnetic resonance of hydrogen atoms from the average value and the shift data.

Then, the pulse setting unit 102 corrects the center frequency of the RF pulse so as to agree with the center frequency of the magnetic resonance of hydrogen atoms at the temperature at the fourth timing. After that, under the control of the sequence controller 56, the MR signal for each slice in the fourth time phase of dynamic imaging is acquired in the same manner as described above.

[Step S9] The MRI apparatus 20 reconstructs the image data for all the slices in all the time phases.

That is, the image reconstruction unit 90 obtains the k-space data from the k-space database 92 and reconstructs image data by performing image reconstruction processing including Fourier transformation on the obtained k-space data. The image reconstruction unit 90 stores the reconstructed image data in the image database 94.

The image processing unit 96 obtains the image data from the image database 94 and generates image data for two-dimensional display by performing predetermined image processing on the obtained image data. The image processing unit 96 stores the image data for two-dimensional display in the storage device 66.

The process described above is performed for k-space data for each slice. After that, the images of all the slices in all the time phases are displayed on the monitor of the display device 64 in the form of moving image.

This is the end of the description of an operation of the MRI apparatus 20 according to this embodiment.

As described above, according to this embodiment, the relationship between the variation of the temperature of the gradient magnetic field coil unit 26 and the shift of the center frequency of the magnetic resonance of hydrogen atoms is previously recorded as the shift data in the data storing unit 100 by the temperature coefficient acquisition sequence. Then, during imaging, the variation of the temperature of the gradient magnetic field coil unit 26 is measured at a plurality of timings, and the center frequency of the RF pulse is corrected as required based on the shift data so as to agree with the center frequency of the resonance of hydrogen atoms at the varied temperature.

Thus, even if the center frequency of the resonance of hydrogen atoms shifts because of heat generated by the gradient magnetic field coils, the center frequency of the RF pulse approximately agrees with the shifted center frequency of the resonance of hydrogen atoms, and therefore, the resulting image has high quality. This is because the effect of the fat suppression prepulse or the like does not degrade over an extended imaging time, since the center frequency of the fat suppression prepulse or the like is corrected to follow the shift of the center frequency of the magnetic resonance of hydrogen atoms due to the temperature variation as described above with reference to FIG. 6. As the imaging time becomes longer, the temperature becomes higher. However, according to this embodiment, temperature measurement and correction of the center frequency are repeatedly performed even after start of the main scan, so that the fat suppression prepulse or the like can be kept effective.

According to this embodiment, since the variation of the center frequency of the resonance of hydrogen atoms can be followed, the cooling facility for the gradient magnetic field coil unit 26 can be minimized, and therefore, the cooling cost can be reduced. Furthermore, since the variation of the center frequency of the resonance of hydrogen atoms can be followed, a gradient magnetic field coil unit with high thermal conductivity (that is, low thermal capacity) can be used in the MRI apparatus 20.

Furthermore, according to this embodiment, a user can set the timing of measurement of the temperature of the gradient magnetic field coil unit 26 or the frequency of correction of the center frequency of the RF pulse (Step S1).

As an alternative, table data that describes the relationship between the center frequency and the absolute temperature may be previously stored, and the center frequency may be corrected based only on the table data and the temperature measured during the main scan without relying on any temperature difference. However, it is more preferable to correct the center frequency based on the difference between the temperature measured during the prescan and the temperature measured during the main scan as described above. This is because, in general, the center frequency is provisionally determined based on the result of the prescan. That is, the center frequency measured during the main scan can be more effectively corrected by calculating the required shift of the center frequency from the center frequency measured during the prescan based on the temperature difference between during the prescan and during the main scan.

Supplementary Notes for an Embodiment

[1] Although an example has been described in which the center frequency is modified in the four-time-phase dynamic imaging, the present invention is not limited to such an implementation and can be applied to other types of imaging. For example, temperature may be measured after a vacant span each time a data acquisition operation for one slice is completed. In this case, the center frequency is then corrected based on the measurement result, and after that, a data acquisition operation for the next slice is performed. The data acquisition operation referred to herein begins with application of a prepulse or an excitation pulse for data acquisition and ends with acquisition (collection) of MR signals and does not include image reconstruction.

In the spin echo method, the data acquisition operation including application of the excitation pulse and the refocusing pulse and acquisition of the MR signal is repeated as many times as the number of phase encode step numbers. In this case, the center frequency may be corrected for each phase encode step. That is, the temperature of the gradient magnetic field coil unit 26 may be measured at a timing after acquisition of the MR signal for a phase encoding and before application of the excitation pulse for the next phase encoding, and the center frequency may be corrected based on the measurement result before start of application of the excitation pulse for the next phase encoding.

Alternatively, in imaging of one slice, the center frequency of the pulse transmitted may be altered between when the excitation pulse and the refocusing pulse are transmitted and when the MR signals are collected (read out). In this case, since the phase varies, phase correction is preferably performed in image reconstruction.

[2] As a supplementation to the note [1] described above, for example, in the case where dynamic imaging is performed in such a manner that T1 weighted images for four time phases are first taken and then T2 weighed images for four time phases are taken, the MRI apparatus 20 may be configured as described below. That is, the input device 62, the display device 64, the pulse setting unit 102 and other units may be configured to correct the center frequency before imaging for each time phase over all the time phases (the four time phases for the T1 weighed images and the four time phases for the T2 weighed images) when "ON" is selected and inputted.

In the case described above, for example, the four time phases for the T1 weighted images can be regarded as one imaging sequence, and the four time phases for the T2 weighted images can be regarded as another imaging sequence. In such a case, if a completion of an imaging (in one imaging sequence) is used as a trigger, the center frequency can be corrected at the first to sixth timings described below.

Firstly, the center frequency can be corrected at a timing during a vacant span after completion of the imaging for the first time phase in the T1 weighted imaging sequence and before start of the imaging for the second time phase in the T1 weighted imaging sequence.

Secondly, the center frequency can be corrected at a timing during a vacant span after completion of the imaging for the second time phase in the T1 weighted imaging sequence and before start of the imaging for the third time phase in the T1 weighted imaging sequence.

Thirdly, the center frequency can be corrected at a timing during a vacant span after completion of the imaging for the third time phase in the T1 weighted imaging sequence and before start of the imaging for the fourth time phase in the T1 weighted imaging sequence.

Fourthly, the center frequency can be corrected at a timing during a vacant span after completion of the imaging for the first time phase in the T2 weighted imaging sequence and before start of the imaging for the second time phase in the T2 weighted imaging sequence.

Fifthly, the center frequency can be corrected at a timing during a vacant span after completion of the imaging for the second time phase in the T2 weighted imaging sequence and before start of the imaging for the third time phase in the T2 weighted imaging sequence.

Sixthly, the center frequency can be corrected at a timing during a vacant span after completion of the imaging for the third time phase in the T2 weighted imaging sequence and before start of the imaging for the fourth time phase in the T2 weighted imaging sequence.

That is, in the case described above, for example, the center frequency is not corrected immediately before start of the imaging for the first time phase in the T1 weighted imaging sequence and during the vacant span after completion of the imaging for the fourth time phase in the T1 weighted imaging sequence and before start of the imaging for the first time phase in the T2 weighted imaging sequence.

Compared with the other timings, omitting the correction of the center frequency at the timing immediately before start of the imaging for the first time phase in the T1 weighted imaging sequence has fewer disadvantages. This is because this is a timing after the scout images are displayed and the region of interest or the like is set, and it is considered that the temperature of the gradient magnetic field coil unit 26 has not significantly risen at this timing considering the number of images having been taken at that time.

[3] This embodiment can be applied to not only the dynamic imaging but also other imaging sequences, such as diffusion weighted imaging. In the following, a case where this embodiment is applied to the diffusion weighted imaging will be described as an example.

In this case, for example, imaging of a reference set of slices is performed under the conditions that a motion probing gradient pulse (referred to as an MPG pulse hereinafter) is not applied and a b-factor is zero. The number of slices in each set is fixed for all sets of slices.

Then, the b-factor is set at a first value, and imaging of the first to N-th sets of slices is performed by applying the MPG pulse. The vector of the MPG pulse differs among the first to N-th sets. That is, the sets of slices are successively imaged by changing the vector of the MPG pulse after imaging of the first set is completed and before imaging of the second set is started, and so on.

Then, the b-factor is set at a second value, and imaging of the first to N-th sets of slices is performed by applying the MPG pulse in the same manner as described above. The vectors of the MPG pulse for the first to N-th sets are the same as those used when the b-factor is set at the first value.

Then, the b-factor is set at a third value, and imaging of the first to N-th sets of slices is performed by applying the MPG pulse in the same manner.

In the case of such an imaging sequence, the imaging time generally tends to be long, and therefore, the temperature of the gradient magnetic field coil unit 26 is expected to rise significantly.

Thus, for example, in the imaging group in which the b-factor is set at the first value, temperature is measured between sets of slices. Since the temperature measurement can be performed instantaneously, it can be performed between sets of slices, whether or not there is a vacant span between the sets. An RF pulse having the center frequency corrected based on the measured temperature and the shift data is used for imaging of the set subsequent to the temperature measurement.

In the above description, the temperature measurement and the correction of the center frequency are performed for each set. However, this is only an example. For example, the temperature measurement and the correction of the center frequency may be performed every two or three sets. In any case, the center frequency of the RF pulse is preferably fixed during imaging of one set in which the vector of the MPG pulse and the b-factor are fixed.

[4] In this embodiment, an example has been described in which the center frequency of the RF pulse is corrected based on the shift of the center frequency of the magnetic resonance of hydrogen atoms at a reference time, which is the time when the temperature sensors 70A to 70D detect temperature. However, the embodiment of the present invention is not limited to such an implementation. For example, the temperature of the gradient magnetic field coil unit 26 at a time subsequent to the reference time, which is the time of temperature measurement, may be predicted.

More specifically, the temperature during the next imaging sequence (in particular, at the time in the vicinity of acquisition of the MR signal at the center of the k-space) may be predicted based on the result of measurement of the temperature variation in the gradient magnetic field coil unit 26 after start of operation of the MRI apparatus 20, and the center frequency of the RF pulse may be corrected based on the predicted temperature and the shift data before start of the next imaging sequence.

[5] In this embodiment, an example has been described in which the temperature of the gradient magnetic field coil unit 26 is not measured during some of the vacant spans between the time phases (the vacant span before the third time phase of the four time phases) according to the input information. However, the embodiment of the present invention is not limited to such an implementation. For example, the input setting screen for inputting the timing of temperature measurement may not be displayed, and the pulse setting unit 102 may completely automatically determine the timing of temperature measurement and the timing of correction of the center frequency of the RF pulse. For example, the temperature of the gradient magnetic field coil unit 26 may be measured during all the vacant spans between the time phases, and the center frequency of the RF pulse may be corrected based on the measured temperature and the shift data.

[6] Although an example has been described in which the shift of the center frequency of the magnetic resonance of hydrogen atoms is calculated, and the center frequency of the RF pulse is corrected based on the shift, the embodiment of the present invention is not limited to such an implementation. As a technically equivalent alternative, the center frequency of the magnetic resonance of hydrogen atoms itself may be estimated, and the center frequency of the RF pulse may be corrected based on the estimated center frequency.

[7] An example has been described in which an average value of four values, $\Delta TpA\_T1$, $\Delta TpB\_T1$, $\Delta TpC\_T1$, and $\Delta TpD\_T1$ is calculated in Steps S5, S6, and S8, and the shift of the center frequency is determined from the average value and the shift data. However, the present invention is not limited to such an implementation.

Considering the size of the gradient magnetic field coil unit 26, the temperature in the gradient magnetic field coil unit 26 is not uniform when heat is generated as a result of the main scan. For example, consider a case where many temperature sensors spaced apart from each other in the X-, Y-, and Z-axis directions of the apparatus coordinate system are disposed in the gradient magnetic field coil unit 26.

In this case, the temperature difference (which corresponds to the above-described $\Delta TpA\_T1$ or the like) detected by each temperature sensor is multiplied by a weight coefficient in such a manner that the higher the weight coefficient, the closer to the imaging cross section the temperature sensor is. Then, the temperature differences multiplied by the respective weight coefficients are summed. Then, the sum of the temperature differences is divided by the number of temperature sensors to calculate the weighted average temperature difference. The shift of the center frequency can also be determined from the weighted average temperature difference and the shift data.

[8] An example has been described in which as the MRI apparatus 20 the RF receiver 48 is disposed outside the gantry that includes the static magnetic field magnet 22, the shim coil 24, the gradient magnetic field coil unit 26 and the like (see FIG. 1). However, the embodiment of the present invention is not limited to such an implementation. The RF receiver 48 may be included in the gantry.

Specifically, for example, an electronic circuit board that is equivalent to the RF receiver 48 may be disposed in the gantry. Then, the MR signal, which is an analog electrical signal converted from the electromagnetic wave by the receiving RF coil 28, may be amplified by a pre-amplifier in the electronic circuit board, the amplified signal may be outputted to the outside of the gantry as a digital signal and inputted to the sequence controller 56. In outputting the signal to the outside of the gantry, an optical communication cable is preferably used to transmit the signal in the form of an optical digital signal because the effect of external noise is reduced, for example.

[9] Correspondences between terms used in the claims and terms used in the embodiment described above will be described. Note that the correspondences described below are just some of possible interpretations for reference and should not be construed as limiting the present invention.

The entire functions of the static magnetic field magnet 22, the shim coil 24, the gradient coil 26, the RF coils 28 and the control system 30 (see FIG. 1) that generate image data of the object P by imaging with application of gradient magnetic fields and RF pulses is an example of an imaging unit described in the claims.

The temperature sensors 70A to 70D are an example of a temperature measuring unit described in the claims.

The function of the display device 64 of displaying a screen for accepting input information for setting the timing of temperature measurement and the function of the input device 62 of receiving input information on the timing of temperature measurement are examples of an input unit described in the claims.

[10] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus, comprising:
    an MRI gradient magnetic field coil unit configured to generate a gradient magnetic field in an imaging space according to a current supplied thereto;
    at least one temperature sensor configured to measure a temperature of the MRI gradient magnetic field coil unit at least two times at different timings to detect at least one coil unit temperature difference between said different timings;
    a data store in which shift data have been recorded in advance of measurements by the temperature sensor, the shift data indicating a shift of a center frequency of hydrogen atom nuclear magnetic resonance (NMR) in the imaging space as a function of variation of gradient magnetic field coil unit temperature;
    a pulse setting unit configured to acquire a measurement result from the temperature sensor, to determine an estimated shift of the hydrogen atom NMR center frequency using the detected variation of temperature and the stored shift data, and to correct an RF pulse center frequency based on the estimated shift; and
    an imaging unit configured to transmit the corrected RF pulse to receive magnetic resonance signals from an object in the imaging space, and to generate image data of the object based on the received magnetic resonance signals.

2. The magnetic resonance imaging apparatus according to claim 1, wherein:
    the at least one temperature sensor includes a plurality of temperature sensors disposed in the gradient magnetic field coil unit to measure the temperature of the gradient magnetic field coil unit; and
    the shift data prescribes, for each temperature sensor, a ratio between (a) variation of gradient magnetic field coil unit temperature based on temperatures measured by the temperature sensors and (b) shift of the hydrogen atom NMR center frequency.

3. The magnetic resonance imaging apparatus according to claim 2, wherein:
    the pulse setting unit is configured to use an average value of temperature differences detected by the temperature sensors as the temperature variation of the gradient magnetic field coil unit.

4. The magnetic resonance imaging apparatus according to claim 3, further comprising:
    an input unit configured to receive input information that prescribes timing of temperature measurement by the at least one temperature sensor,
    wherein the at least one temperature sensor is configured to measure gradient magnetic field coil unit temperature at an on-timing prescribed by the input information to perform temperature measurement; and
    the pulse setting unit is configured to determine the estimated center frequency shift and correct the RF pulse center frequency based on the estimated shift after the on-timing.

5. The magnetic resonance imaging apparatus according to claim 4, further comprising:
    a display unit configured to display a plurality of timings as candidates for temperature measurement timing input,
    wherein the input unit is configured to permit operator selection of on-timing from among the plurality of timings displayed on the display unit.

6. The magnetic resonance imaging apparatus according to claim 3, wherein:
    the imaging unit is configured to perform dynamic imaging which includes a vacant span between each of plural time phases and to collect, in each time phase, magnetic resonance signals for constructing a plurality of images;
    the temperature sensors are configured to detect the gradient magnetic field coil unit temperature during the vacant span; and
    the pulse setting unit is configured to correct the RF pulse center frequency during the vacant span.

7. The magnetic resonance imaging apparatus according to claim 3, wherein:
    the imaging unit is configured to successively perform diffusion weighted imaging per set of imaging sequences by changing a vector of a motion probing gradient pulse for each set of imaging sequences, each set of imaging sequences including acquisition of magnetic resonance signals for constructing a plurality of images;
    the temperature sensors are configured to detect the gradient magnetic field coil unit temperature between each set; and
    the pulse setting unit is configured to correct the RF pulse center frequency between each set.

8. The magnetic resonance imaging apparatus according to claim 1, wherein:
the imaging unit is configured to perform dynamic imaging in which each of plural time phases includes acquisition of magnetic resonance signals for constructing a plurality of images.

9. The magnetic resonance imaging apparatus according to claim 1, wherein:
the imaging unit is configured to perform dynamic imaging which includes a vacant span between each of plural time phases and to collect, in each time phase, magnetic resonance signals for constructing a plurality of images;
the at least one temperature sensor is configured to detect the temperature of the gradient magnetic field coil unit during the vacant span; and
the pulse setting unit is configured to correct the RF pulse center frequency during the vacant span.

10. The magnetic resonance imaging apparatus according to claim 9, wherein:
the at least one temperature sensor is configured to detect the gradient magnetic field coil unit temperature during all vacant spans respectively during the dynamic imaging; and
the pulse setting unit is configured to respectively correct the RF pulse center frequency in all vacant spans in the dynamic imaging.

11. The magnetic resonance imaging apparatus according to claim 9, wherein:
the at least one temperature sensor is configured to detect the gradient magnetic field coil unit temperature between (a) collection of the magnetic resonance signal for constructing each image and (b) collection of the magnetic resonance signal for constructing a next image; and
the pulse setting unit is configured to correct the RF pulse center frequency between (i) collection of the magnetic resonance signal for constructing each image and (ii) collection of the magnetic resonance signal for constructing the next image.

12. The magnetic resonance imaging apparatus according to claim 1, wherein:
the imaging unit is configured to perform diffusion weighted imaging which includes application of a motion probing gradient pulse.

13. The magnetic resonance imaging apparatus according to claim 1, wherein:
the imaging unit is configured to successively perform diffusion weighted imaging per set of imaging sequences by changing a vector of a motion probing gradient pulse for each set of imaging sequences, each set of imaging sequences including acquisition of magnetic resonance signals for constructing a plurality of images;
the at least one temperature sensor is configured to detect the gradient magnetic field coil unit temperature between each set; and
the pulse setting unit is configured to correct the RF pulse center frequency between each set.

14. The magnetic resonance imaging apparatus according to claim 1, further comprising:
an input unit configured to receive input information that prescribes a timing of temperature measurement by the at least one temperature sensor,
wherein the at least one temperature sensor is configured to measure the gradient magnetic field coil unit temperature at an on-timing prescribed by the input information to perform temperature measurement; and the pulse setting unit is configured to determine the estimated shift and to correct the RF pulse center frequency based on the estimated shift after the on-timing.

15. The magnetic resonance imaging apparatus according to claim 14, further comprising:
a display unit configured to display a plurality of timings as candidates for temperature measurement timing input,
wherein the input unit is configured to permit operator selection of the on-timing from among the plurality of timings displayed on the display unit.

16. The magnetic resonance imaging apparatus according to claim 14, further comprising:
a display unit configured to display a plurality of timings as candidates for temperature measurement timing input,
wherein the input unit is configured to permit operator selection of a timing not to perform temperature measurement from among a plurality of timings displayed on the display unit.

17. The magnetic resonance imaging apparatus according to claim 14, wherein:
the input unit is configured to permit operator selection of a timing to perform temperature measurement from among a plurality of timings displayed on the display unit, and
the pulse setting unit is configured to perform (a), after an off-timing, calculation of the estimated shift at the off-timing based on a result of measurement performed by the at least one temperature sensor before the off-timing and (b) correction of the RF pulse center frequency based on the estimated shift,
the off-timing being a timing prescribed by the input information not to perform temperature measurement.

18. The magnetic resonance imaging apparatus according to claim 1, wherein:
the RF pulse includes a prepulse suppressing the magnetic resonance signal from fat tissue.

19. A magnetic resonance imaging (MRI) method comprising:
measuring a temperature of an MRI gradient magnetic field coil unit, which generates a gradient magnetic field in an imaging space according to a current supplied thereto, at least two times at different timings to detect at least one coil unit temperature difference between said different timings;
recalling from memory, previously stored shift data indicating shift of a center frequency of hydrogen atom nuclear magnetic resonance (NMR) in the imaging space as a function of variation of the gradient magnetic field coil unit temperature;
determining an estimated shift of the hydrogen atom NMR center frequency using the detected variation of temperature and the stored shift data,
correcting an RF pulse center frequency based on the estimated shift; and
generating image data of an object based on magnetic resonance signals by transmitting the center frequency corrected RF pulse and receiving magnetic resonance signals from the object in the imaging space.

20. The magnetic resonance imaging apparatus according to claim 1, wherein:
the at least one temperature sensor is configured to measure a temperature of the gradient magnetic field coil unit as an initial temperature before start of imaging; and
the pulse setting unit is configured to set a provisional RF pulse center frequency based on the initial temperature, and to then later determine the estimated center frequency shift based on a current variation of measured temperature from the earlier measured initial temperature and the stored shift data.

21. The magnetic resonance imaging apparatus according to claim 20, further comprising:
a cooling control device configured to circulate coolant in the gradient magnetic field coil unit,
wherein
the at least one temperature sensor is configured to measure the initial temperature at a timing when the temperature of the gradient magnetic field coil unit converges to a predetermined value; and
the pulse setting unit is configured to correct an RF pulse center frequency by shifting the provisional center frequency by the estimated shift amount.

* * * * *